United States Patent [19]
Bey, Jr. et al.

[11] Patent Number: 5,264,798
[45] Date of Patent: Nov. 23, 1993

[54] AUTONULLING AC BRIDGE USING DIFFERENTIAL AND INTEGRATION FEEDBACK

[75] Inventors: Paul P. Bey, Jr., Temple Hills, Md.; Thomas L. Fare, Washington, D.C.

[73] Assignees: The United States of America as represented by the Secretary of the Navy, Washington, D.C.; Geo-Centers, Inc., Newton Centre, Mass.

[21] Appl. No.: 783,904

[22] Filed: Oct. 29, 1991

[51] Int. Cl.$^5$ .................. G01R 17/06; G01N 27/02
[52] U.S. Cl. ........................... 324/725; 324/98; 324/610; 324/651; 324/443; 307/257
[58] Field of Search ............... 324/610, 651, 657, 706, 324/725, 98, 99 R, 443; 307/257, 262; 328/155

[56] References Cited

U.S. PATENT DOCUMENTS

| | | | |
|---|---|---|---|
| 3,473,177 | 10/1969 | Ito | 324/651 |
| 3,474,334 | 10/1969 | Yokoyama et al. | 324/651 |
| 3,593,126 | 7/1971 | May | 324/651 |
| 4,315,210 | 2/1982 | Michel et al. | 324/57 R |

FOREIGN PATENT DOCUMENTS 1286126  11/1968  U.S.S.R. ...................... 324/99 R

Primary Examiner—Gerard R. Strecker
Assistant Examiner—Diep Do
Attorney, Agent, or Firm—Oblon, Spivak, McClelland, Maier & Neustadt

[57] ABSTRACT

A self-contained autonulling bridge circuit based on phase-sensitive detection of an impedance to be measured is described. The system utilizes a feedback structure to control a variable impedance in order to establish the null of the bridge. The system utilizes a voltage-variable impedance having both resistance and capacitance and provides the phase sensitive relationship in the control means in order to provide highly accurate measurement of an unknown test impedance. The ability to measure small changes in impedance provides particularly useful application to the area of biological sensor impedance measurement or electrochemical impedance measurement using silicon-based devices.

13 Claims, 3 Drawing Sheets

AUTONULLING AC BRIDGE USING DIFFERENTIAL AND INTEGRATION FEEDBACK

BACKGROUND OF THE INVENTION

1. Field of the Invention

The present invention is addressed to a circuit for the measurement of the impedance of biological and electrochemical systems and more particularly the accurate measurement of the resistance, separate from the total impedance of the systems.

2. Discussion of Background

Biological and electrochemical systems are electrically modeled as a combination of a resistor and a capacitor connected in parallel. The independent determination of either the resistance or the capacitance determines the state of the system. Two examples of this include resistance measured in temperature sensors and capacitance measured in pressure sensors. Therefore it is important to have an impedance sensor that can transduce both phase and magnitude so that independent changes in resistance and capacitance can be separately observed.

It is an inherent characteristic of biological and electrochemical systems that the impedances have significant capacitance, although, in many instances, the characteristic of interest is the resistance. For example, electrodermal measurements or electrochemical "cells" used in monitoring specific reactions and ion concentration require transducing only the resistance. When the capacitive reactance (the capacitive component of impedance) is large compared to the resistive component, accurate measurement of both magnitude and phase of the impedance is required in order to resolve small variations in the resistance. In laboratory environments, lock-in-amplifiers or impedance analyzers are used to make such measurements of voltages across the unknown impedance. These instruments are used in conjunction with voltage dividers to obtain highly sensitive and accurate measurements.

The prior art automated impedance measurment devices use completely analog voltage divider designs which give outputs corresponding to in-phase and quadrature-phase components. Although these devices offer phase sensitivity, the sampling which is required for the analog device is subject to noise and may thus require additional filtering which increases the cost and complexity of such systems.

SUMMARY OF THE INVENTION

It is an object of the present invention to provide an improved bridge network system for accurate measurement of small impedance variations.

The objects of the present invention are defined by a bridge network which uses differential measurements to increase noise immunity and provides a measurement which is directly proportional to the unknown impedance for accurate measurement of small changes in impedance components.

It is also an object of the present invention to implement an autonulling AC bridge which is designed for microfabrication and is compatible with silicon-based electrode sensors and micromachined silicon devices.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
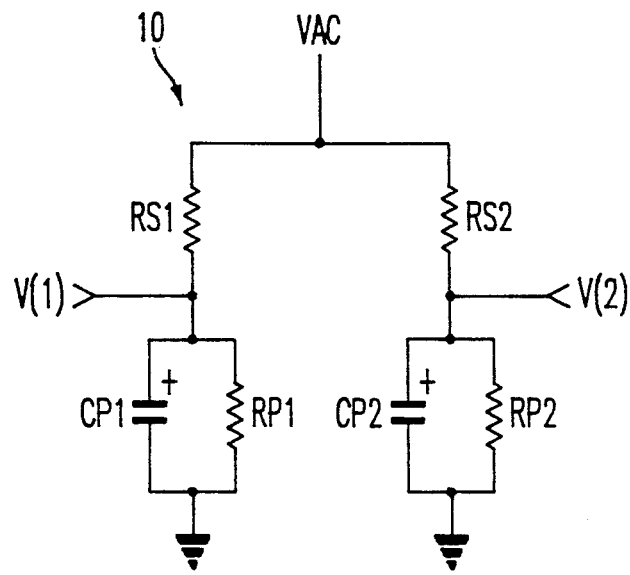
FIG. 1 is a bridge network to be used in conjunction with the construction of the autonulling bridge of the present invention.

Referring now to the drawings, wherein like reference numerals designate identical or corresponding parts throughout the several views, and more particularly to FIG. 1 thereof, a bridge network 10 for improved impedance measurement contains resistances RS1 in series with the parallel combination of RP1 and CP1 and resistance RS2 in series with the parallel combination of CP2 and RP2 which are voltage-variable and operated in their linear regions. Capacitance CP1 and resistance RP1 represent the unknown AC impedance which is to be measured, such as an electrochemical or biological system. The approach of the bridge diagram of FIG. 1 utilizes differential measurements which provide greater noise immunity than a voltage divider scheme.

The system operates by applying an AC reference voltage (VAC) as shown in FIG. 1 and the current from this applied voltage is divided into the branches according to the impedance encountered in each branch. If RS1=RS2, the difference in voltage from V(1) to V(2) across the bridge will be zero if and only if the impedances of RP1 and CP1 in parallel equals the impedance of RP2 and CP2 in parallel. Thus both CP1 and RP1 must correspond identically to CP2 and RP2.

With this bridge system, a design circuit can be constructed for an autonulling AC bridge which is suitable for use with impedance-transducing devices. The bridge circuitry of FIG. 1 is especially well designed for systems which measure small changes in impedance, primarily because the difference developed across the bridge can be greatly amplified. Previous bridge measuring devices required a manual adjustment to determine values of unknown impedances that in some cases could take seconds or even minutes to balance.

Figure 2:
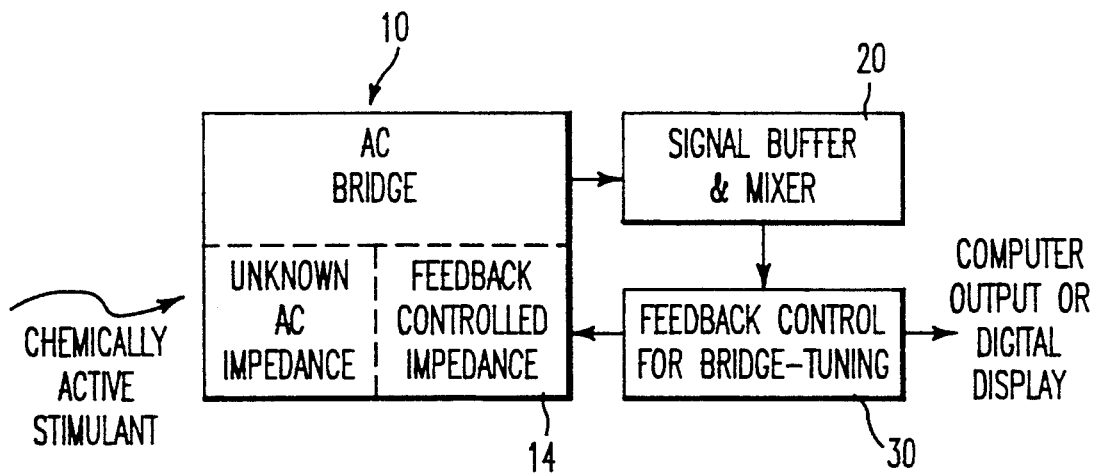
FIG. 2 is a block diagram of the autonulling AC bridge of the present invention.

A self-contained device constructed in accordance with the block diagram of FIG. 2 provides the autonulling AC bridge and provides it in such a way that the only additional requirement is a digital volt meter to measure the output voltages. Furthermore the device constructed in accordance with FIG. 2 provides a stable measurement of an impedance variation in less than one tenth of a second. The voltages are calibrated to the outputs for known impedances.

Figure 3:
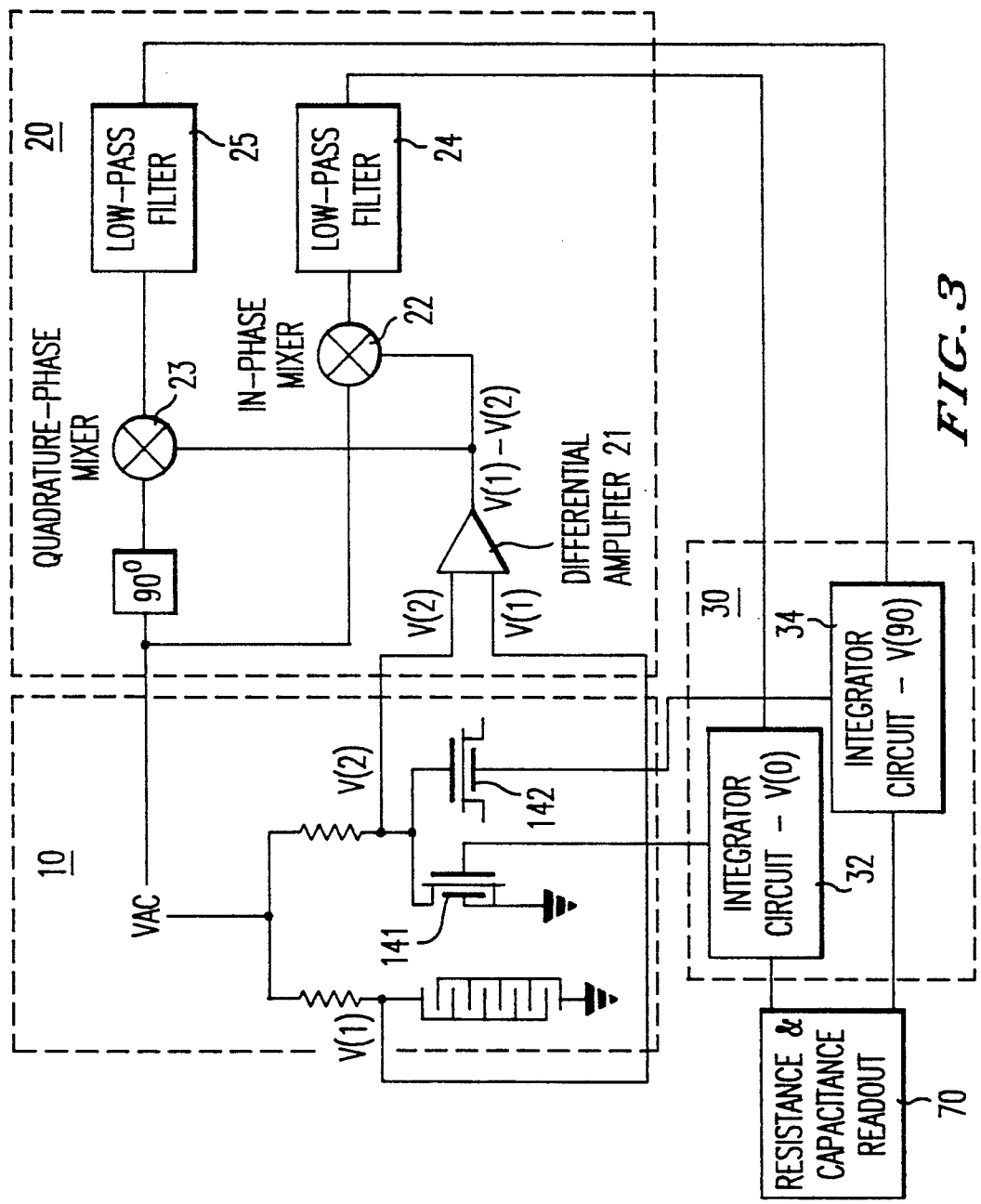
FIG. 3 is a detailed block diagram of the autonulling AC bridge of FIG. 2.

The bridge nulling circuit of FIG. 2, in block diagram form, is an analog feedback network which established a stable null across the bridge for a wide range of resistive and capacitive values with a minimum of supporting hardware. The AC bridge 10 of FIG. 2 corresponds to the FIG. 1 while the signal buffer and mixer 20 provide a DC output for feedback control 30 for use in conjunction with the feedback controlled impedance portion 14 of the bridge 10. Small changes in resistance and capacitance in one arm of the bridge are compensated independently using a discrete voltage-variable resistor (VVR) and voltage-variable capacitor (VVC) connected in parallel in the opposite arm until nulled. The feedback system in FIG. 3 provides a measurement which is directly proportional to the unknown impedance rather than providing some non-linear signal derived from a voltage divider. The DC output for feedback control can be digitally displayed such as with a voltmeter.

FIG. 3 provides a schematic block diagram for a particular realization of the circuit of FIG. 2 utilizing a MOSFET 141 for the voltage-variable resistor and a MOSCAP (Metal-oxide semiconductor capacitor) for the voltage-variable capacitor 142 portion of the feedback control impedance 14 of FIG. 2. These voltage-variable resistor and capacitor 141, 142, in turn, correspond to RP2 and CP2 of FIG. 1.

The signal indicating the difference between the bridge node voltages V(1)–V(2) is obtained from the differential amplifier 21 and fed to two separate multipliers 22 and 23, respectively. Multiplier 22 multiplies the difference voltage with the in-phase reference signal while multiplier 23 multiplies the difference signal with a quadrature-phase reference signal. The outputs from these two mixers 22 and 23 are passed through the low-pass filters 24 and 25 respectively to remove AC components. The outputs of the filters 24 and 25 constitute DC signals which are fed to respective integrators 32 and 34. The integrator 32 which receives the in-phase signal from filter 24 outputs a signal to the gate of a MOSFET 141 while the output from the integrator 34 receiving the quadrature-phase DC signal controls MOSCAP (metal oxide semiconductor capacitor) 142. The feedback signals from these integrators 32, 34 drive the respective MOSFET 141 and MOSCAP 142 until the difference voltage from the bridge becomes zero. When the difference voltage is zero, the feedback loop is stabilized at a particular point because the phase and magnitude of the difference signals V(1)–V(2) are zero and the integrator outputs remain at constant values. The integrator circuits 32, 34 provide the output to the resistance and capacitance readout 70 which is, for example, a voltmeter.

The feedback voltage to the discrete elements can be used to transduce signals from pressure, temperature or chemical sensors or in the optimization of control systems. Because the VVR 141 and VVC 142 can be integrated into silicon this particular bridge is especially well-suited for microfabrication and is readily compatible with silicon-based electrode sensors and micromachined silicon devices. Electrodes which can be fabricated with the VVR (MOSFET) and the VVC (MOSCAP) directly enable testing of chemically-active systems deposited on the electrodes. Some of these chemically-active systems include phospholipid membranes; inorganic films with ion-selective additives; and neuro and muscular cells.

Quite obviously fabrication of this structure in silicon is important because this facilitates the measurement of AC impedances of synthetic membrane biosensors and biological systems which are prone to noise pick-up. One of the contributors to noise is the minute perturbation in the surroundings which can cause dramatic changes to the systems' steady state. The advances in lithographic techniques allow for the patterning of living organisms and other chemically sensitive systems on hydrophilic surfaces. For this reason the bridge design of the present invention as disclosed by the FIG. 3 provides a unique method for transducing changes in the systems' function which is accomplished in real time. This enables the fabrication of large arrays of these bridges which can be individually sampled. These arrays can be used so that they all have the same chemical-sensitive systems in order to increase reliability of the detection of one component or they can also be used in a number of combinations of chemical-sensitive films to enable the detection of mixtures of chemical species.

Utilizing the autonulling AC bridge of FIG. 3, the phase-sensitive measurement is taken differentially across the bridge nodes, V(1)–V(2) which allows for high noise rejection. Any noise which is local to the integrated silicon device can be subtracted and therefore reduced because the interference is common to nodes in close proximity to each other.

The following examples illustrate variations on the basic circuitry of FIG. 2 using different types of phase sensitive feedback components and operations involving only the resistance or only the capacitance portion of the feedback control impedance:

EXAMPLE 1

Figure 4:
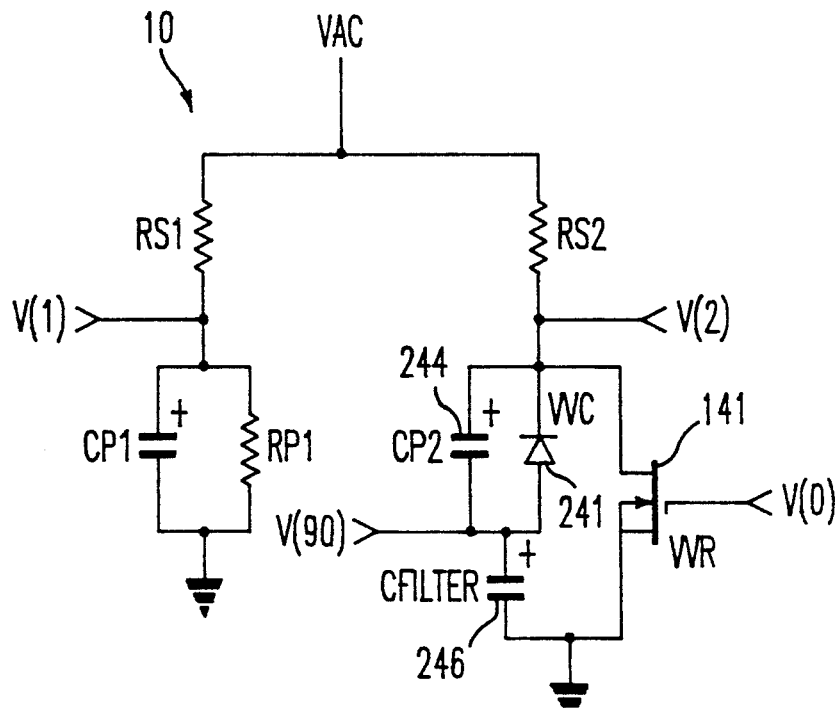
FIG. 4 illustrates a tuning diode as the VVC (voltage-variable capacitor) and a MOSFET as the VVR (voltage-variable resistor).

An AC bridge was configured using discrete elements of FIG. 1 wherein the values of the resistances RS1 and RS2 were chosen to be equal as were the capacitance CP1 and CP2. The resistance in the unknown branch was a fixed resistor, RP1, and in the control branch aVR, RP2. A 1 KHz 100 millivolt AC voltage was applied to the bridge (VAC) using an HP3312A function generator. The difference voltage across the bridge, V(1)–V(2), was fed into the differential input of an EG & G 5208 lock-in-amplifier (LIA) and a TTL signal in synch with VAC was input as the reference signal. The LIA displays values of in-phase and quadrature-phase components of the difference signal and also provides voltage output signals proportional to the in-phase and quadrature-phase at output terminals. The in-phase voltage from the LIA output was integrated and the output of the integrator V(O) was connected directly to the gate of the VVR (MOSFET) in the control branch of the bridge. When the feedback loop was connected, the difference voltage on the LIA was nulled to within ±10 microvolts of zero which demonstrates the operation of the real component feedback loop. Furthermore, a 20 pF fixed capacitor was added in parallel with the original capacitor CP1 in the unknown branch. A tuning-diode 241, as the VVC, was connected in series with large filtering capacitor 242 to ground and was placed in parallel, with the fixed capacitor CP2 (244) in the control branch as shown in FIG. 4. The filter capacitor 242 was chosen to be large enough so that it would be a negligible impedance in the series combination. The quadrature-phase feedback voltage V(90) was generated in the same manner as the in-phase feedback and fed to the node between the VVC (capacitance diode) 241 and the filter capacitor 242. When this loop was connected, the junction capacitance of the tuning diode drove the bridge circuit to a null. In-phase and quadrature-phase feedback resulted in a null condition across the bridge indicated by the differential voltage on the LIA of the same magnitude as in the first part of this example.

EXAMPLE 2

In this example an analog multiplier ("modified" LIA) was used as the phase-sensitive feedback component. The modification involved the use of the analog multipliers to mix the difference voltage with in-phase and quadrature-phase reference signals, respectively. A 555 timer IC was used to produce a TTL square wave with variable frequency. A 50% duty cycle was necessary for this application. Because the duty cycle of the 555 oscillator varies with the frequency, the duty cycle must be adjusted by feeding the signal into a negative edge-triggered flip-flop in toggle mode. This gave rise to a transition on every negative edge of the 555 output therefore providing 50% duty cycle at half the original frequency. The signal was fed both into a negative edge triggered flip-flop and a positive edge-triggered flip-flop simultaneously. The output of these two flip-flops was one fourth the frequency of the original 555 signal and precisely 90° out of phase with each other producing the in-phase and quadrature-phase reference signals. A self-contained signal generator was also used to produce a "shaped" since wave from the in-phase square wave discussed above by integrating the square wave twice which made this version of the device a completely stand-alone prototype. The outputs of each multiplier were fed into a low-pass filter which generated a DC signal proportional to the phase between the two multiplied signals. The DC signals were then integrated. In this example the outputs of the integrators were used as phase-sensitive feedback signals and drove the VVR and VVC. The operation of the bridge was monitored by use of an oscilloscope attached at the difference voltage output. The configuration also yielded a less than 10 microvolt difference signal similar to the previous example.

EXAMPLE 3

In this example a standard Wheatstone bridge with the modified LIA was constructed using only the in-phase feedback loop. This example is the same as example 2 with the exception that only a resistance was used in the unknown branch and only the MOSFET was used in the control branch. The in-phase feedback signal was connected to the gate of the MOSFET bringing the bridge to a null condition. In this example the stable operation of a stand-alone model of the device was demonstrated as well as the phase-sensitive extraction of the difference voltage with respect to the in-phase signal.

EXAMPLE 4

In this example the system of the modified LIA of Example 2 was used but only a capacitance was used in the unknown branch and only a tuning diode in series with a filtering capacitor was used in the control branch. The quadrature-phase feedback signal was connected to the node between the diode and the filter capacitor bringing the bridge to a null condition. This once again demonstrated the accurate phase-sensitive extraction of the difference voltage with respect to the quadrature-phase signal.

EXAMPLE 5

The system of Example 2 was configured with both feedback loops connected but the RP1 was replaced with a fixed resistor and a trim pot whose full swing was 5% of the fixed resistor. This trim pot and the fixed resistor were connected in series while a fixed capacitor was used for CP1. When the trim pot was varied the voltage on the MOSFET gate tracked the variation. Then small capacitors in the range of the tuning diode were placed in parallel with CP1 causing the quadrature-phase feedback to track the variations accordingly. It was observed that the variation seen in the control voltages agreed with the component variations observed for resistance-only or capacitance-only cases of Examples 3 and 4. This provided for verification of the small signal approximation by perturbing the unknown values when the system was at a null.

The feedback bridge circuit of the present invention of FIG. 3 provides significant advantages which make it particularly suitable for many sensor applications.

One of the first advantages is that the voltage across the bridge reaches a point of stability when the voltage is zero so that the voltage can be amplified providing higher accuracy near the null point. Differential measurements also yield a high noise rejection because common noise is subtracted from both sides of the bridge.

A second advantage is that the feedback control is phase sensitive therefore making it stable for a wide range of operating frequencies (frequency selective). It is thus possible to detect small changes in in-phase and quadrature-phase components of the differential voltage which are each used independently to null the bridge using integral feedback. The output of the integrators directly drive the control components to the value of the resistance and the capacitive reactance in the unknown branch forcing a null condition across the bridge. The range of operation of the discrete voltage-control components is in their respective linear regions, therefore yielding direct correlations with the unknown values by a set of calibration curves which relate the integrator output voltages to resistance or capacitance values.

A third advantage to the feedback bridge circuit is that the voltage-variable components in the balancing scheme are discrete metal oxide semiconductor (MOS) devices, making it ideal for microfabrication. This enables the incorporation of the scheme with a micron-scale topology. Noise-rejection of the system is enhanced because the differential measurement on the device is subject to the same noise in the environment at this scale.

Figure 5:
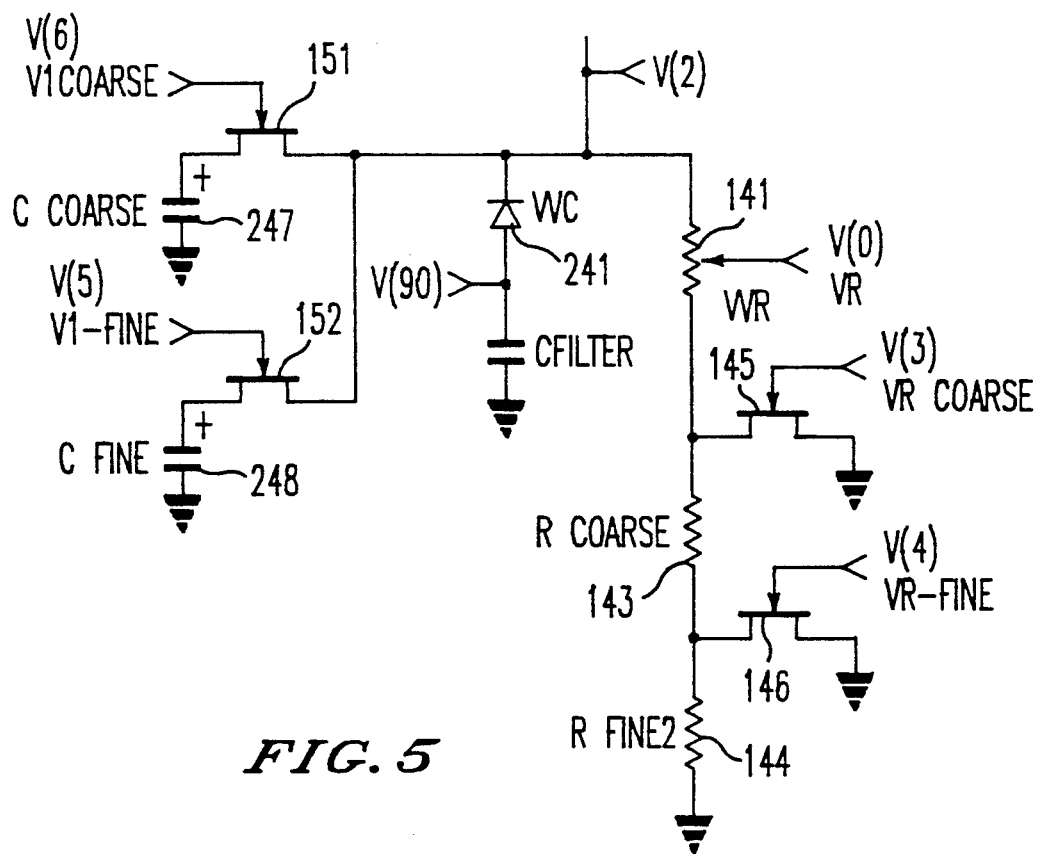
FIG. 5 illustrates switching control to extend range of operation.

Further enhancements of the range of operation of the AC bridge of the present invention can be obtained by switching precision components into the control branch. This can be done by adding fixed capacitors in parallel with the VVC (MOSCAP) as well as switching fixed resistors in series with the VVR (MOSFET) giving rise to a wide range of operation as illustrated in FIG. 5. This can be accomplished for the fine and coarse capacitors 248 and 247 by using respective switching FETs 151 and 152 between the upper node of the VVC and the upper node of the associated capacitor 247, 248 whose other node is connected to ground. Many such capacitors could be connected in this manner and only capacitors whose connecting FETs are in the "on" state will be added to the control capacitance. With respect to the resistance, the bottom node of the VVR is connected to ground through a switching FET 145 as well as an indefinite series of resistances (shown as resistance 143, 144) each also connected to ground through an FET, except the last resistance 144 which is connected directly to ground. In this case only one switching FET is on at any one time leaving any resistor below that particular FET out of the series connection. The combination of these two methods for switching fixed resistors in and out of the control branch yield a very versatile method of "coarse and fine" adjustment which is practical in the nulling algorithm. The capacitance banking can be done in "coarse and fine" increments corresponding to the values connected to the VVC. An algorithm to determine which components to switch-in to approach the range of the VVR and VVC has been developed and analyzed over wide ranges of both resistance and capacitance using only the sense of the phase and the sense of the magnitude.

The control of the nulling range can be scaled as follows. When RS1 equals RS2, the impedance of the unknown components have to be within the range of the voltage control components. By varying the value of RS1 with respect to RS2, the range of values of RP1 and CP1 which can be nulled by RP2 and CP2 is varied proportionally with RP2 being varied directly and CP2 being varied inversely. Variations in RS1 or RS2 can be obtained by connecting resistances with switching FETs in series and parallel combinations with each resistance RS1 and RS2. The respective values can be changed stepwise by applying appropriate gate voltages to the switching FETs turning them either fully on or fully off. Thus there is a digital described method for selecting a resistance range in a stepwise manner, but as with the actual nulling resistor RP2, the use of an analog gate voltage could be used to vary device RS1 and RS2 continuously.

Control for more accurate nulling is accomplished by using an automatic gain control (AGC) differential amplifier. The AGC can be used to increase the gain of the difference signal as the difference signal magnitude becomes small. Because of the time constant of the integrators in the feedback, this magnitude will vary at frequencies near the operating frequency of the bridge and thus the time constant of the AGC must be increased in order to enable the feedback to stabilize before either increasing or decreasing the gain. This is carried out by connecting a peak-detector to the amplified difference signal to set the gain of an instrumentation amplifier.

Increased phase sensitivity can be accomplished by the use of a band-selective or band-pass filter on the difference signal from the bridge which aids in the isolation of the operating frequency of the bridge and therefore enhances the noise immunity of the mixing process.

Another feature which can be expanded based upon the FIG. 3 embodiment of the present invention is the use of the circuit for impedance matching on front-end amplifiers. Using the circuit of FIG. 3, connected to a source and a receiver, it is possible to adjust the input impedance of the receiver to match the output impedance of the source. Using the matched impedances, power transfer from source to receiver is maximized. The circuit can similarly be used for automatic gain control applications using a single frequency as the gain control standard. In these instances, the gain of the front-end amplifier is matched to the magnitude of the input signal at a particular frequency.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An autonulling bridge circuit system for measuring impedance changes, comprising:
    an AC bridge circuit including two current dividing branches with a first branch including a test impedance to be measured and a second branch including a feedback controlled impedance means wherein each of sad first and second branches receives an alternating current first reference voltage, said bridge circuit further including a first and a second output voltage means each connected to a respective one of said first and second branches;
    signal buffer means responsive to said first reference voltage and the outputs of said first and second voltage output means to provide at least one phase relate output signal said signal buffer means including means for amplifying the difference between said first and second output voltage and means for providing said at least one phase related output signal as DC output signal; and
    feedback control means including an integrator means for receiving said at least one phase related DC output signal and outputting a respective at least one feedback output signal for controlling said feedback controlled impedance, said feedback control means also outputting a display signal indicating the impedance of said test impedance, wherein said signal buffer means includes an in-phase mixer for receiving both said first reference voltage and the output of said amplifier means and a quadrature-phase mixer for receiving both 90° shifted first reference voltage and the output of said amplifier means and wherein said in-phase mixture and said quadrature-phase mixture respectively provide a first and second mixture output fed to a respective first and second low pass filter and wherein the outputs of said respective first and second low pass filters provide two phase related DC output signals to said feedback control means.

2. The system according to claim 1, wherein said feedback controlled impedance includes a MOSFET as a voltage-variable resistance.

3. The apparatus according to claim 1, wherein said feedback controlled impedance includes a voltage-variable resistor and a voltage-variable capacitor.

4. The apparatus according to claim 3, wherein said voltage-variable resistor is a MOSFET and said voltage-variable capacitor is a tuning-diode capacitor.

5. The system according to claim 3, wherein said voltage-variable capacitor is a MOSCAP.

6. The system according to claim 1, wherein said feedback control means includes two integrator circuit means receiving respective ones of said two phase-related DC outputs and wherein said two integrator circuits output respective signals to said feedback controlled impedance.

7. The system according to claim 6, wherein the filtered output of said in-phase mixer is fed to a first integrator circuit which outputs a signal to the gate of a MOSFET of said feedback control impedance and wherein a second integrator circuit receives a filtered output of said quadrature-phase mixer in order to provide a second feedback control signal provided to a tuning-diode capacitor or MOSCAP of said feedback control impedance.

8. The system according to claim 1, wherein said test impedance results from application of a chemically-active system deposited on at least one impedance member.

9. A sensor impedance detector, comprising:

a bridge network including two branches with a first branch including a sensor impedance to be measured and the second branch including feedback controlled impedance means wherein each of said first and second branches receive an alternating current reference voltage and said bridge circuit further including a first and second output means each connected to a respective one of said first and second branches;

feedback control means responsive to the output of said first and second output means and responsive to said first reference voltage to provide a phase-sensitive control signal output to said feedback controlled impedance means and said feedback control means further including a means for providing a second output indicating the measured value of said sensor impedance, wherein said feedback control means includes a difference amplifier means responsive to said first and second voltage output to provide a difference signal, said feedback control means further including a mixing means responsive to said reference signal and said difference signal to provide at lease one dc phase sensitive detection signal to said feedback controlled impedance means.

10. A detector according to claim 9 wherein said feedback controlled impedance means includes a voltage-variable resistor and voltage-variable capacitor.

11. The detector according to claim 10 wherein said voltage-variable capacitor is a MOSCAP and wherein said voltage-variable resistor is a MOSFET.

12. The detector according to claim 10, wherein said voltage-variable capacitor is a tuning diode.

13. The detector according to claim 9, wherein said sensor impedance has a chemically-active system deposited on at least one impedance member.

* * * * *